US008078287B2

(12) United States Patent
Liu et al.

(10) Patent No.: US 8,078,287 B2
(45) Date of Patent: Dec. 13, 2011

(54) HIS BUNDLE MAPPING, PACING, AND INJECTION LEAD

(75) Inventors: Lili Liu, White Bear Lake, MN (US); Randy Westlund, Minneapolis, MN (US); Steven D. Girouard, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 1130 days.

(21) Appl. No.: 11/760,294

(22) Filed: Jun. 8, 2007

(65) Prior Publication Data
US 2007/0233216 A1    Oct. 4, 2007

Related U.S. Application Data

(62) Division of application No. 10/745,302, filed on Dec. 23, 2003, now Pat. No. 7,245,973.

(51) Int. Cl.
*A61N 1/05* (2006.01)

(52) U.S. Cl. .................................. 607/127; 607/122

(58) Field of Classification Search .................. 607/120, 607/122, 126–128; 600/381, 509
See application file for complete search history.

(56) References Cited

U.S. PATENT DOCUMENTS

| 3,614,955 | A | 10/1971 | Mirowski |
| 3,804,098 | A | 4/1974 | Friedman |
| 3,866,615 | A | 2/1975 | Hewson |
| 3,911,928 | A | 10/1975 | Lagergren |
| 3,949,757 | A | 4/1976 | Sabel |
| 4,026,303 | A | 5/1977 | Babotai |
| 4,030,508 | A | 6/1977 | Thalen |
| 4,057,067 | A | 11/1977 | Lajos |
| 4,106,512 | A | 8/1978 | Bisping |
| 4,136,703 | A | 1/1979 | Wittkampf |
| 4,154,247 | A | 5/1979 | O'Neill |
| 4,217,913 | A | 8/1980 | Dutcher |
| 4,258,725 | A | 3/1981 | O'Neill |
| 4,278,093 | A | 7/1981 | Lafortune et al. |

(Continued)

FOREIGN PATENT DOCUMENTS

DE    2827595    4/1979

(Continued)

OTHER PUBLICATIONS

"Coating Process for Composite Implants", *Medical Materials Update*, vol. 1, No. 12, (Jan. 1995), pp. 1 and 4.

(Continued)

*Primary Examiner* — Carl H Layno
*Assistant Examiner* — Jessica Sarcione
(74) *Attorney, Agent, or Firm* — Faegre & Benson LLP

(57) ABSTRACT

A cardiac rhythm management system includes a lead assembly for intracardiac mapping, pacing, and drug delivery. The lead assembly includes an implantable endocardial lead having a proximal end for connection to an implantable cardiac rhythm management device and a distal end for disposal in an intracardiac region. The lead includes a pacing-sensing electrode and a drug delivery device, both located at or near the distal end. A lumen is within and extends throughout the lead, with an opening at or near the proximal end and another opening at or near the distal end. The lumen provides for access to the intracardiac region by a steerable stylet and a hollow needle, one at a time. The steerable stylet allows for electrophysiological mapping of the intracardiac region. The hollow needle allows for delivery of chemical, biochemical, and/or biological substance to the intracardiac region.

8 Claims, 9 Drawing Sheets

U.S. PATENT DOCUMENTS

| | | | |
|---|---|---|---|
| 4,282,885 A | 8/1981 | Bisping | |
| 4,289,144 A | 9/1981 | Gilman | |
| 4,311,153 A | 1/1982 | Smits | |
| 4,332,259 A | 6/1982 | McCorkle, Jr. | |
| 4,393,883 A | 7/1983 | Smyth et al. | |
| 4,402,329 A | 9/1983 | Williams | |
| 4,437,474 A | 3/1984 | Peers-Trevarton | |
| 4,458,677 A | 7/1984 | McCorkle, Jr. | |
| 4,458,695 A | 7/1984 | Peers-Trevarton | |
| 4,463,765 A | 8/1984 | Gold | |
| 4,469,104 A | 9/1984 | Peers-Trevarton | |
| 4,497,326 A | 2/1985 | Curry | |
| 4,540,236 A | 9/1985 | Peers-Trevarton | |
| 4,549,548 A | 10/1985 | Wittkampf et al. | |
| 4,559,951 A | 12/1985 | Dahl et al. | |
| 4,567,901 A | 2/1986 | Harris | |
| 4,570,642 A | 2/1986 | Kane et al. | |
| 4,577,643 A | 3/1986 | Beranek | |
| 4,602,645 A | 7/1986 | Barrington et al. | |
| 4,603,705 A | 8/1986 | Speicher et al. | |
| 4,624,265 A | 11/1986 | Grassi | |
| 4,624,266 A | 11/1986 | Kane | |
| 4,627,439 A | 12/1986 | Harris | |
| 4,633,880 A | 1/1987 | Osypka et al. | |
| 4,643,201 A | 2/1987 | Stokes | |
| 4,646,755 A | 3/1987 | Kane | |
| 4,649,937 A | 3/1987 | DeHaan et al. | |
| 4,649,938 A | 3/1987 | McArthur | |
| 4,664,113 A | 5/1987 | Frisbie et al. | |
| 4,667,686 A | 5/1987 | Peers-Travarton | |
| 4,721,115 A | 1/1988 | Owens | |
| 4,784,161 A | 11/1988 | Skalsky et al. | |
| 4,799,486 A | 1/1989 | DuFault | |
| 4,799,493 A | 1/1989 | DuFault | |
| 4,819,647 A | 4/1989 | Byers et al. | |
| 4,819,661 A | 4/1989 | Heil, Jr. et al. | |
| 4,819,662 A | 4/1989 | Heil, Jr. et al. | |
| 4,876,109 A | 10/1989 | Mayer et al. | |
| 4,886,074 A | 12/1989 | Bisping | |
| 4,922,607 A | 5/1990 | Doan et al. | |
| 4,922,927 A | 5/1990 | Fine et al. | |
| 4,924,881 A | 5/1990 | Brewer | |
| 4,953,564 A | 9/1990 | Berthelsen | |
| 4,967,766 A | 11/1990 | Bradshaw | |
| 4,972,848 A | 11/1990 | DiDomenico et al. | |
| 4,994,078 A | 2/1991 | Jarvik | |
| 5,002,067 A | 3/1991 | Berthelsen et al. | |
| 5,007,864 A | 4/1991 | Stutz, Jr. | |
| 5,016,646 A | 5/1991 | Gotthardt et al. | |
| 5,050,601 A | 9/1991 | Kupersmith et al. | |
| 5,056,516 A | 10/1991 | Spehr | |
| 5,063,932 A | 11/1991 | Dahl et al. | |
| 5,076,285 A | 12/1991 | Hess et al. | |
| 5,083,564 A | 1/1992 | Scherlag | |
| 5,092,879 A | 3/1992 | Jarvik | |
| 5,129,404 A | 7/1992 | Spehr et al. | |
| 5,144,960 A | 9/1992 | Mehra et al. | |
| 5,152,299 A | 10/1992 | Soukup | |
| 5,174,289 A | 12/1992 | Cohen | |
| 5,179,962 A | 1/1993 | Dutcher et al. | |
| 5,181,511 A | 1/1993 | Nickolls et al. | |
| 5,223,226 A | 6/1993 | Wittmar et al. | |
| 5,242,430 A | 9/1993 | Arenas et al. | |
| 5,255,693 A | 10/1993 | Dutcher et al. | |
| 5,259,394 A | 11/1993 | Bens | |
| 5,259,395 A | 11/1993 | Li | |
| 5,275,620 A | 1/1994 | Darby et al. | |
| 5,282,845 A | 2/1994 | Bush et al. | |
| 5,300,108 A | 4/1994 | Rebell et al. | |
| 5,304,219 A | 4/1994 | Chernoff et al. | |
| 5,306,292 A | 4/1994 | Lindegren | |
| 5,320,642 A | 6/1994 | Scherlag | |
| 5,324,327 A | 6/1994 | Cohen | |
| 5,336,252 A | 8/1994 | Cohen | |
| 5,342,414 A | 8/1994 | Mehra | |
| 5,344,439 A | 9/1994 | Otten | |
| 5,358,516 A | 10/1994 | Myers et al. | |
| 5,366,496 A | 11/1994 | Dahl et al. | |
| 5,374,286 A | 12/1994 | Morris | |
| 5,381,790 A | 1/1995 | Kanesaka | |
| 5,393,929 A | 2/1995 | Yagihashi | |
| 5,405,373 A | 4/1995 | Petersson et al. | |
| 5,411,544 A | 5/1995 | Mar et al. | |
| 5,425,755 A | 6/1995 | Doan | |
| 5,433,735 A | 7/1995 | Zanakis et al. | |
| 5,439,391 A | 8/1995 | McEtchin et al. | |
| 5,447,533 A | 9/1995 | Vachon et al. | |
| 5,447,534 A | 9/1995 | Jammet | |
| 5,456,706 A | 10/1995 | Pless et al. | |
| 5,456,708 A | 10/1995 | Doan et al. | |
| 5,466,253 A | 11/1995 | Doan | |
| 5,476,497 A | 12/1995 | Mower et al. | |
| 5,476,499 A | 12/1995 | Hirschberg | |
| 5,476,501 A | 12/1995 | Stewart et al. | |
| 5,476,502 A | 12/1995 | Rubin | |
| 5,492,119 A | 2/1996 | Abrams | |
| 5,500,008 A | 3/1996 | Fain | |
| 5,514,172 A | 5/1996 | Mueller | |
| 5,515,848 A | 5/1996 | Corbett, III et al. | |
| 5,522,874 A | 6/1996 | Gates | |
| 5,524,338 A | 6/1996 | Martynuik et al. | |
| 5,527,344 A | 6/1996 | Arzbaecher et al. | |
| 5,531,780 A | 7/1996 | Vachon | |
| 5,545,201 A | 8/1996 | Helland et al. | |
| 5,549,109 A * | 8/1996 | Samson et al. | 600/381 |
| 5,554,178 A | 9/1996 | Dahl et al. | |
| 5,571,163 A | 11/1996 | Helland | |
| 5,578,068 A | 11/1996 | Laske et al. | |
| 5,593,433 A | 1/1997 | Spehr et al. | |
| 5,628,778 A | 5/1997 | Kruse et al. | |
| 5,628,779 A | 5/1997 | Bornzin et al. | |
| 5,634,829 A | 6/1997 | Kerul | |
| 5,634,899 A | 6/1997 | Shapland et al. | |
| 5,674,272 A | 10/1997 | Bush et al. | |
| 5,674,274 A | 10/1997 | Morgan et al. | |
| 5,709,753 A | 1/1998 | Olson et al. | |
| 5,716,390 A | 2/1998 | Li | |
| 5,720,099 A | 2/1998 | Parker et al. | |
| 5,755,766 A | 5/1998 | Chastain et al. | |
| 5,769,881 A | 6/1998 | Schroeppel et al. | |
| 5,772,693 A | 6/1998 | Brownlee | |
| 5,782,760 A * | 7/1998 | Schaer | 600/381 |
| 5,782,898 A | 7/1998 | Dahl et al. | |
| 5,807,306 A | 9/1998 | Shapland et al. | |
| 5,851,227 A | 12/1998 | Spehr | |
| 5,871,529 A | 2/1999 | Bartig et al. | |
| 5,871,531 A | 2/1999 | Struble | |
| 5,876,399 A | 3/1999 | Chia et al. | |
| 5,876,431 A | 3/1999 | Spehr et al. | |
| 5,916,214 A | 6/1999 | Cosio et al. | |
| 5,925,045 A | 7/1999 | Reimels et al. | |
| 5,935,159 A | 8/1999 | Cross, Jr. et al. | |
| 5,941,868 A | 8/1999 | Kaplan et al. | |
| 5,944,710 A | 8/1999 | Dev et al. | |
| 5,964,795 A | 10/1999 | McVenes et al. | |
| 5,972,416 A | 10/1999 | Reimels et al. | |
| 6,007,476 A | 12/1999 | Wascher et al. | |
| 6,024,739 A | 2/2000 | Ponzi et al. | |
| 6,059,726 A | 5/2000 | Lee et al. | |
| 6,086,582 A | 7/2000 | Altman et al. | |
| 6,096,069 A | 8/2000 | Bischoff | |
| 6,123,084 A | 9/2000 | Jandak et al. | |
| 6,141,594 A | 10/2000 | Flynn et al. | |
| 6,165,164 A | 12/2000 | Hill et al. | |
| 6,236,887 B1 | 5/2001 | Ben-Haim et al. | |
| 6,254,573 B1 | 7/2001 | Haim et al. | |
| 6,309,370 B1 | 10/2001 | Haim et al. | |
| 6,345,204 B1 | 2/2002 | Scheiner et al. | |
| 6,358,247 B1 | 3/2002 | Altman et al. | |
| 6,363,286 B1 | 3/2002 | Zhu et al. | |
| 6,416,510 B1 | 7/2002 | Altman et al. | |
| 6,463,334 B1 | 10/2002 | Flynn et al. | |
| 6,468,263 B1 | 10/2002 | Fischell et al. | |
| 6,505,082 B1 | 1/2003 | Scheiner et al. | |
| 6,512,957 B1 * | 1/2003 | Witte | 607/116 |
| 6,540,725 B1 | 4/2003 | Ponzi | |
| 6,544,270 B1 | 4/2003 | Zhang | |

| | | |
|---|---|---|
| 6,547,787 B1 | 4/2003 | Altman et al. |
| 6,560,489 B2 | 5/2003 | Hauck |
| 6,575,931 B1 | 6/2003 | Ponzi |
| 6,585,716 B2 | 7/2003 | Altman |
| 6,623,473 B1 | 9/2003 | Ponzi |
| 6,623,474 B1 | 9/2003 | Ponzi |
| 6,702,744 B2 | 3/2004 | Mandrusov et al. |
| 6,702,777 B2 | 3/2004 | Haim et al. |
| 6,810,286 B2 | 10/2004 | Donovan et al. |
| 6,855,124 B1 | 2/2005 | Gonzalez et al. |
| 6,905,476 B2 | 6/2005 | Ponzi |
| 6,909,920 B2 | 6/2005 | Lokhoff et al. |
| 6,915,169 B2 | 7/2005 | Flynn et al. |
| 6,931,286 B2 | 8/2005 | Sigg et al. |
| 7,077,842 B1 * | 7/2006 | Cosman .................... 606/41 |
| 7,174,222 B2 * | 2/2007 | Tockman et al. ............ 607/122 |
| 7,245,973 B2 | 7/2007 | Liu et al. |
| 7,392,095 B2 | 6/2008 | Flynn et al. |
| 7,400,931 B2 | 7/2008 | Mandrusov et al. |
| 7,460,914 B2 | 12/2008 | Mandrusov et al. |
| 2001/0031986 A1 | 10/2001 | Hauck |
| 2001/0044619 A1 | 11/2001 | Altman |
| 2002/0010492 A1 | 1/2002 | Donovan et al. |
| 2002/0016615 A1 | 2/2002 | Dev et al. |
| 2002/0022863 A1 | 2/2002 | Hauck |
| 2002/0026228 A1 | 2/2002 | Schauerte |
| 2002/0058981 A1 | 5/2002 | Zhu et al. |
| 2002/0183720 A1 | 12/2002 | Hill et al. |
| 2003/0032938 A1 | 2/2003 | Altman |
| 2003/0069625 A1 | 4/2003 | Ley et al. |
| 2003/0093104 A1 | 5/2003 | Bonner et al. |
| 2003/0109914 A1 | 6/2003 | Westlund et al. |
| 2003/0113303 A1 | 6/2003 | Schwartz |
| 2003/0125615 A1 | 7/2003 | Schwartz |
| 2003/0129750 A1 | 7/2003 | Schwartz |
| 2003/0163184 A1 | 8/2003 | Scheiner et al. |
| 2003/0171723 A1 | 9/2003 | Ponzi |
| 2003/0195470 A1 | 10/2003 | Ponzi |
| 2004/0122484 A1 | 6/2004 | Hatlestad et al. |
| 2004/0186546 A1 | 9/2004 | Mandrusov et al. |
| 2004/0213770 A1 | 10/2004 | Seward et al. |
| 2004/0214182 A1 | 10/2004 | Sharma et al. |
| 2004/0215251 A1 | 10/2004 | Sharma et al. |
| 2005/0267557 A1 | 12/2005 | Flynn et al. |
| 2006/0030810 A1 | 2/2006 | Mandrusov et al. |
| 2008/0262587 A1 | 10/2008 | Flynn et al. |

FOREIGN PATENT DOCUMENTS

| | | |
|---|---|---|
| DE | 3712082 | 10/1988 |
| EP | 0042551 | 12/1981 |
| EP | 0057877 | 8/1982 |
| EP | 0282047 | 9/1988 |
| EP | 0321764 | 6/1989 |
| EP | 0452278 | 10/1991 |
| EP | 0573275 | 12/1993 |
| EP | 519053 | 4/1994 |
| EP | 0612538 | 8/1994 |
| EP | 0620024 | 10/1994 |
| EP | 0672431 | 9/1995 |
| EP | 709111 | 5/1996 |
| FR | 2465489 | 9/1980 |
| FR | 2575925 | 7/1986 |
| FR | 2757773 | 12/1996 |
| GB | 2240721 | 8/1991 |
| WO | WO-92/20401 | 4/1991 |
| WO | WO-94/22525 | 4/1993 |
| WO | WO-97/40883 | 4/1996 |
| WO | WO-96/15665 | 5/1996 |
| WO | WO-0074773 A1 | 12/2000 |

OTHER PUBLICATIONS

"Implant Attaches to Bone by Chemical Bond", *Medical Materials Update*, vol. 4, No. 7, (Aug. 1997),pp. 1 and 5.

"Victrex's PEEK Used for Dialysis Machines", *Medical Material's Update*, vol. 3, No. 3, (Apr. 1996),pp. 1-2.

Al-Khadra, A., et al., "The Role of Electroporation in Defibrillation", *Circulation Research*, 87(9), (Oct. 2000), 797-804.

Avitall, B., "Iontophoretic transmyocardial drug delivery. A novel approach to antiarrhythmic drug therapy.", *Circulation*, 85(4), (Apr. 1992),1582-93.

Barton, A. J., et al., "Bacterial Adhesion to Orthopedic Implant Polymers", *J. Biomed. Mat. Res.*, 30(3), (Mar. 1996),403-410.

Flynn, David M., "Extendable and Retractable Lead Having A Snap-Fit Terminal Connector", U.S. Appl. No. 11/173,664, filed Jul. 1, 2005, 53 Pages.

Genc, S., et al., "Methodology for Locking Feature Selection in Integral Snap-Fit Assembly", *Proceedings of DETC '97, 1997 ASME Engineering Technical Conferences*, (Sep. 1997),1-11.

Ha, S. W., et al., "Plasma-Sprayed Hydroxylapatite Coating on Carbon Fibre Reinforced Thermoplastic Composite Materials", *J. Mater. Sci. Mater. Med.*, vol. 5, No. 6-7, (1994),pp. 481-484.

Jockisch, K. A., et al., "Biological Response to Chopped-Carbon-Fiber-Reinforced Peek", *J. Biomed. Mater. Res.*, vol. 26, No. 2, (1992),pp. 133-146.

Kanno, S., et al., "Establishment of a simple and practical procedure applicable to therapeutic angiogenesis", *Circulation*, 99(20), (May 25, 1999),2682-2687.

Kaye, D. M., et al., "Frequency-dependent activation of a constitutive nitric oxide synthase and regulation of contractile function in adult rat ventricular myocytes", *Circulation Research*, 78(2), (Feb. 1996),217-24.

Knapp, Christopher P., et al., "Snap Fit Terminal Connector", U.S. Appl. No. 09/184,226, filed Nov. 2, 1998, 39.

Labhasetwar, V., et al., "Iontophoresis for Modulation of Cardiac Drug Delivery in Dogs", *Proceedings of the National Academy of Sciences USA*, 92(7), (Mar. 28, 1995),2612-2616.

Lin, T. W., et al., "Glass Peek Composite Promotes Proliferation and Osteocalcin of Human Osteoblastic Cells", *J. Biomed. Mater. Res.*, vol. 36, No. 2, (1997),pp. 137-144.

MacNair, R., et al., "The Response of Primary Rat and Human Osteoblasts and an Immortalized Rat Osteoblast Cell Line to Orthopaedic Materials: Comparative Sensitivity of Several Toxicity Indices", *J. Mater. Sci. Mater. Med.*, vol. 8, No. 2, (1997),pp. 105-111.

Mansourati, J., et al., "Left ventricular-based pacing in patients with chronic heart failure: comparison of acute hemodynamic benefits according to underlying heart disease", *Eur J Heart Fail.*, 2(2), (Jun. 2000),195-9.

Meyer, M. R., et al., "Long-Term Durability of the Interface FRP Composites After Exposure to Simulated Physiologic Saline Environments", *J. Biomed. Mater. Res.*, vol. 28, No. 10, (1994),pp. 1221-1231.

Morrison, C., et al., "In Vitro Biocompatibility Testing of Polymers for Orthopaedic Implants Using Cultured Fibroblasts and Osteoblasts", *Biomaterials*, vol. 16, No. 13, (1995),pp. 987-992.

Qu, J, et al., "HCN2 overexpression in newborn and adult ventricular myocytes: distinct effects on gating and excitability", *Circ. Res.*, vol. 89(1), (Jul. 6, 2001),e8-14.

Qu, J, et al., "Sympathetic innervation alters activations of pacemaker current (If) in rat ventricle", *J. Physiol*, 526 Pt 3, (Aug. 1, 2000),561-569.

Shi, W, et al., "Distribution and prevalence of hyperpolarization-activated cation channel (HCN) mRNA expression in cardiac tissues", *Circ. Res.*, vol. 85(1), (Jul. 9, 1999),e1-6.

Soyer, J., et al., "Experimental Characterisation of a Carbon/PEEK Hip Prothesis in Fatigue", *Chirurgie*, 121, (1996),p. 658-663.

Wenz, L. M., et al., "In Vitro Biocompatibility of Polyetheretherketone and Polysulfone Composites", *J. Biomed. Mater. Res.*, vol. 26, No. 2, (1990),pp. 207-215.

Yu, H., et al., "MinK-related peptide 1: A beta subunit for the HCN ion channel subunit family enhances expression and speeds activation", *Circ. Res.*, 88(12), (Jun. 22, 2001),e84-7.

"U.S. Appl. No. 10/745,302, Notice of Allowance mailed Mar. 12, 2007", 4 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Response filed Jun. 26, 2006 to Non-Final Office Action mailed Mar. 14, 2006", 16 pgs.

"U.S. Appl. No. 10/745,302, Response filed Dec. 14, 2006 to Non-Final Office Action mailed Sep. 14, 2006", 13 pgs.

"U.S. Appl. No. 10/745,302, Response filed Dec. 23, 2005 to Non-Final Office Action mailed Sep. 23, 2005", 15 pgs.

"U.S. Appl. No. 10/745,302, Response filed Sep. 12, 2005 to Restriction Requirement mailed Aug. 12, 2005", 6 pgs.

"U.S. Appl. No. 10/745,302, Restriction Requirement mailed Aug. 12, 2005", 7 pgs.

US 6,875,206, 04/2005, Ponzi (withdrawn)

* cited by examiner

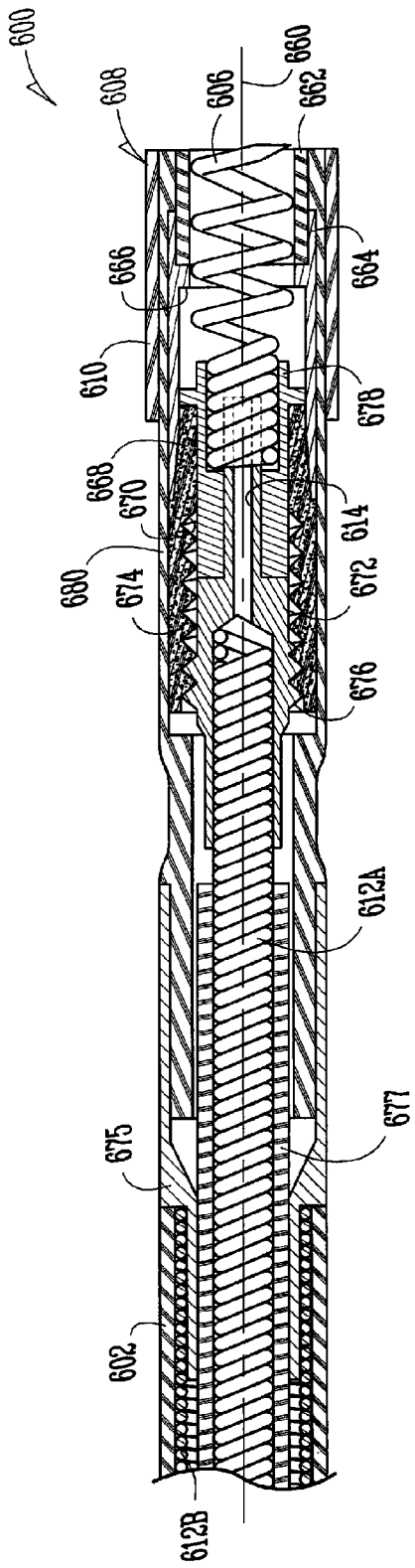
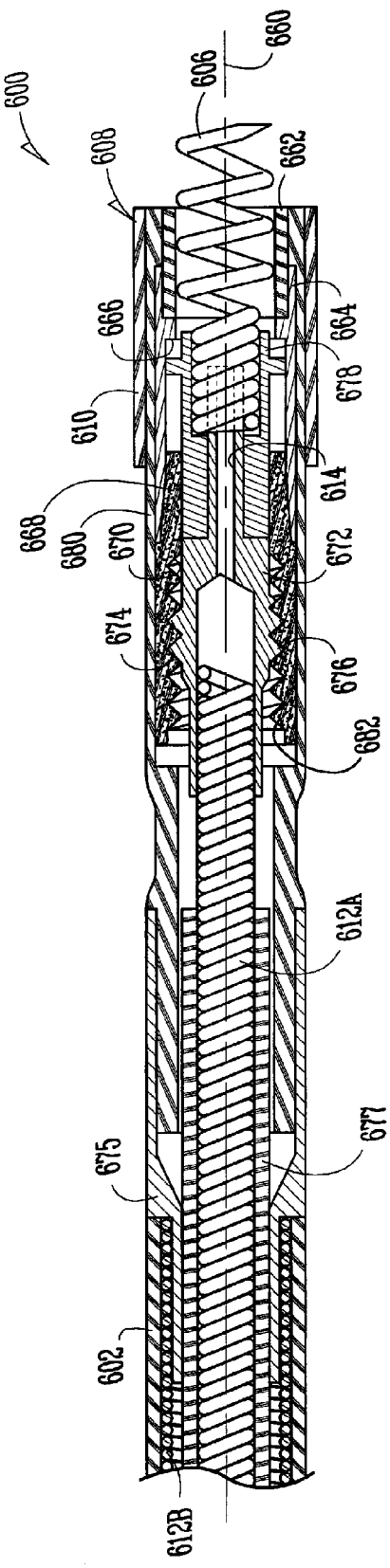

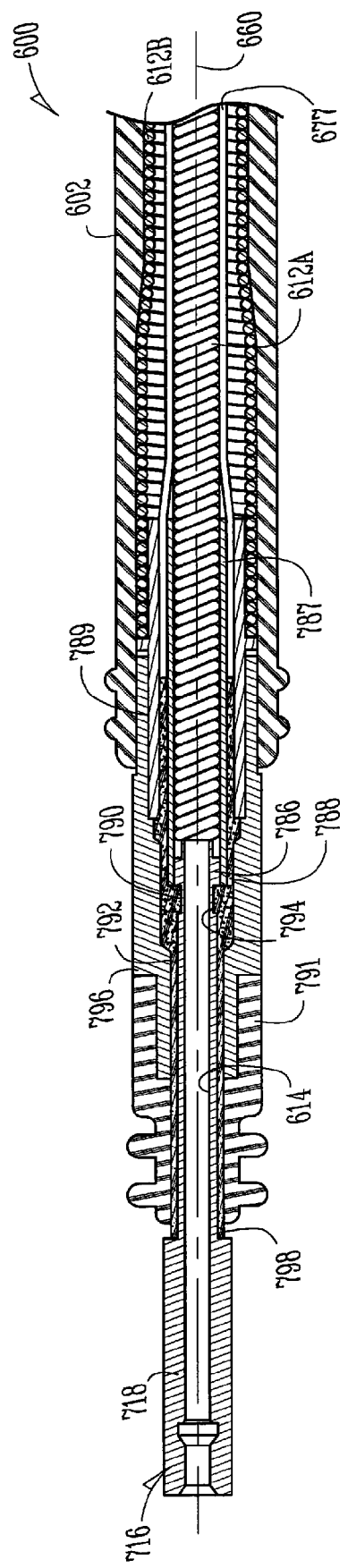

HIS BUNDLE MAPPING, PACING, AND INJECTION LEAD

CROSS-REFERENCE TO RELATED APPLICATIONS

This application is a division of U.S. patent application Ser. No. 10/745,302, filed on Dec. 23, 2003, now issued as U.S. Pat. No. 7,245,973, the specification of which is incorporated herein by reference.

This application is also related to U.S. patent application Ser. No. 10/246,249, "DEVICES AND METHODS TO STIMULATE THERAPEUTIC ANGIOGENESIS FOR ISCHEMIA AND HEART FAILURE," filed on Sep. 18, 2002, now issued as U.S. Pat. No. 7,400,931, assigned to Advanced Cardiovascular Systems, Inc., and U.S. patent application Ser. No. 10/264,494, "EXTENDABLE AND RETRACTABLE LEAD HAVING A SNAP-FIT TERMINAL CONNECTOR," filed Oct. 4, 2002, now issued as U.S. Pat. No. 6,915,169, assigned to Cardiac Pacemakers, Inc., which are hereby incorporated by reference in their entirety.

TECHNICAL FIELD

This document generally relates to cardiac rhythm management systems and particularly, but not by way of limitation, to such systems including a lead assembly for intracardiac electrophysiological mapping, pacing, and drug delivery.

BACKGROUND

A heart is the center of a person's circulatory system. It includes a complex electromechanical system performing two major pumping functions. The heart includes four chambers: right atrium (RA), right ventricle (RV), left atrium (LA), and left ventricle (LV). The left portions of the heart, including the LA and LV, draw oxygenated blood from the lungs and pump it to the organs of the body to provide the organs with their metabolic needs for oxygen. The right portions of the heart, including the RA and RV, draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to excite the muscular tissues of these regions. Coordinated delays in the propagations of these electrical impulses in a normal electrical conduction system cause the various portions of the heart to contract in synchrony to result in efficient pumping functions. A blocked or otherwise abnormal electrical conduction system and/or a deteriorated myocardium cause asynchronized contraction of the heart. Consequently, the person suffers from poor hemodynamic performance, including poor pumping efficiency and diminished blood supply that is usable to satisfy the needs for normal metabolism of the organs.

The heart's electrical conduction system includes internodal pathways between the SA node and the atrioventricular (AV) node, the AV node, the His bundle (also known as the bundle of His, the AV bundle, and the Common bundle), and the Purkinje system including the right bundle branch (RBB) and the left bundle branch (LBB). In the normal heart, the electrical impulses generated from the SA node are conducted to the AV node through the internodal pathways. The propagation of the electrical impulses is delayed in the AV node. The His bundle conducts the electrical impulses from the AV node to the right bundle branch (RBB) and left bundle branch (LBB). The RBB and LBB then conduct the electrical impulses to the RV and LV, respectively, through the Purkinje system, resulting in the contraction of the ventricles.

Damages or depression of the AV node and/or His bundle, known as AV block, impairs the AV conduction, i.e., conduction of the electrical impulses from the RA to the RV and LV. AV block, depending on a degree or severity, can result in excessive delay in the AV conduction, partial blockage of the AV conduction (only some electrical impulses are conducted to the ventricles), or total blockage of the AV conduction (no electrical impulse is conducted to the ventricles). AV block can result from, for example, ischemia, acute myocardial infarction, intoxication, and inflammation. Ablation of the AV node, a surgical procedure performed on patients with atrial fibrillation, also creates total blockage of the AV conduction.

Pacing therapy can restore cardiac function impaired by AV block. One method is His bundle pacing, i.e., delivery of pacing pulses to the His bundle. If conduction system below the AV node remains normal, pacing pulses delivered to the His bundle are conducted through the His bundle and the bundle branches to cause synchronized contraction of the ventricles. In addition, pacing of the His bundle prevents its degeneration, a pathological process that starts with severe or total AV block.

His bundle pacing requires locating a pacing site in or about the His bundle. Unlike conventional atrial and ventricular pacing sites, which can be located by imaging techniques such as fluoroscopy, His bundle cannot be reliably located by imaging. Additionally, chemical, biochemical, and biological therapies may provide further benefits to the condition of the AV node and/or His bundle, as well as other cardiac regions, in addition to His bundle pacing.

Therefore, there is a need for an improved method and system for delivering a therapy to the His bundle.

SUMMARY

A cardiac rhythm management system includes a lead assembly for intracardiac mapping, pacing, and drug delivery. The lead assembly includes an implantable endocardial lead having a proximal end for connection to an implantable cardiac rhythm management device and a distal end for disposal in an intracardiac region. The lead includes a pacing-sensing electrode and a drug delivery device, both located at or near the distal end. A lumen is within and extends throughout the lead, with an opening at or near the proximal end and another opening at or near the distal end. The lumen provides for access to the intracardiac region by a steerable stylet and a hollow needle, one at a time. The steerable stylet allows for electrophysiological mapping of the intracardiac region. The hollow needle allows for delivery of chemical, biochemical, and/or biological substance to the intracardiac region.

In one embodiment, an implantable endocardial lead includes an elongate lead body having a proximal end and a distal end. The lead includes an electrode for sensing cardiac electrical activities and delivering pacing pulses, and a drug delivery device for delivering a pharmaceutical substance. Both the electrode and the drug delivery device are at or near the distal end. A lumen extends throughout the lead body and has one opening at about the proximal end of the lead and another opening at about the distal end of the lead. The lead is for use with an implantable cardiac rhythm management device.

In one embodiment, an implantable endocardial pacing lead assembly includes a steerable stylet and an implantable lead. The steerable stylet has a stylet distal end and a stylet proximal end. It includes a mapping electrode at the stylet distal end, a connector at the stylet proximal end, and a conductor electrically coupled between the mapping electrode and the connector. The implantable lead has an elongate lead body having a lead proximal end and a lead distal end. It includes an electrode at or near the lead distal end for sensing cardiac electrical activities and delivering pacing pulses. A lumen is within and extends through the lead body, with a proximal opening at about the lead proximal end and a distal opening at about the lead distal end. The lumen accommodates at least a portion of the steerable stylet and allows the stylet tip to enter the proximal opening and extend from the distal opening.

In one embodiment, an implantable endocardial pacing lead assembly includes a hollow needle and an implantable lead. The hollow needle allows for intracardiac injection of a therapeutic biological substance. It includes a needle tip and a flexible needle body connected to the needle tip. The implantable lead includes an elongate lead body having a lead proximal end and a lead distal end. It includes an electrode at or near the distal end for sensing cardiac electrical activities and delivering pacing pulses. A lumen is within and extends through the lead body, with a proximal opening at about the lead proximal end and a distal opening at about the lead distal end. The lumen accommodates at least a portion of the needle and allows the needle tip to enter the proximal opening and extend from the distal opening.

In one embodiment, a system providing for access to an intracardiac region includes an implantable medical device and a lead. The implantable medical device includes a pacemaker to deliver pacing pulses to the intracardiac region. The lead includes an elongate lead body, an electrode, a drug delivery device, and a lumen. The elongate lead body has a lead proximal end and a lead distal end. The electrode, located at or near the lead distal end, senses cardiac electrical activities from and delivers pacing pulses to the intracardiac region. The drug delivery device, also located at or near the lead distal end, delivers a pharmaceutical substance to the intracardiac region. The lumen is within and extends through the lead body. The lumen has a proximal opening at about the lead proximal end and a distal opening at about the lead distal end.

In one embodiment, therapies are delivered to an intracardiac region in or about a His bundle. A pharmaceutical substance, including one or more agents preventing degeneration of the intracardiac region, is delivered using an implantable endocardial pacing lead coupled to an implantable pulse generator. Pacing pulses are also delivered to the intracardiac region to enhance an effect of the pharmaceutical substance, using the implantable endocardial pacing lead coupled to the implantable pulse generator.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document. The drawing are for illustrative purposes only, and are neither to scale nor anatomically accurate.

FIG. 6A is an illustration of a specific embodiment of the distal end of the implantable endocardial lead of FIG. 1B.

FIG. 6B is another illustration of the specific embodiment of the distal end of the implantable endocardial lead of FIG. 1B.

FIG. 7 is an illustration of a specific embodiment of the proximal end of the implantable endocardial lead of FIG. 1B.

DETAILED DESCRIPTION

Figure 1A:
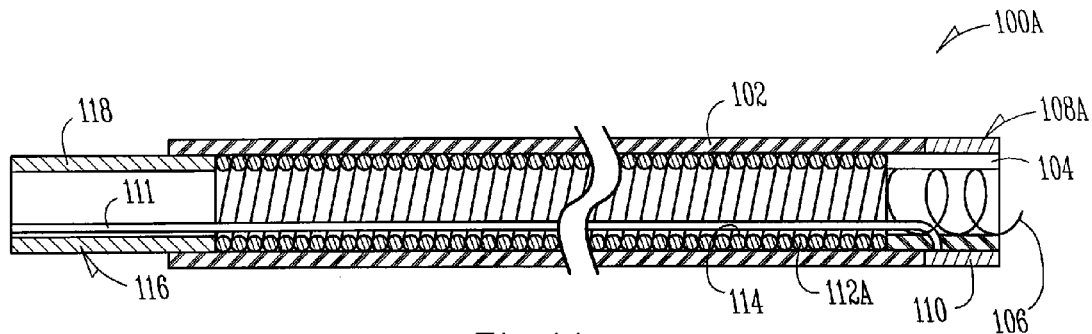
FIG. 1A is an illustration of an embodiment of portions of an implantable unipolar endocardial lead for pacing an intracardiac region.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a cardiac rhythm management (CRM) system including an implantable endocardial lead assembly allowing delivery of electrical therapy, chemical therapy, and biological therapy to an intracardiac region in or about the His bundle. However, it is to be understood that the present methods and apparatuses may be employed to deliver electrical therapy, chemical therapy, and/or biological therapy to other internal organs or regions of a person, including, but not being limited to, other intracardiac regions. After an AV block resulted from an injury to the AV node and/or the His bundle, pacing and drug therapies are delivered to the intracardiac region in or about the His bundle to prevent the His bundle degeneration, prevent the remodeling of the ventricular walls, and maintain a normal or at least tolerable hemodynamic performance. The implantable endocardial lead assembly includes a lead and a mapping stylet for locating of the intracardiac region by electrophysiological mapping, and subsequently, delivering drug and/or electrical therapies to the located intracardiac region. After the intracardiac region has been stabilized and/or conditioned by the drug and/or electrical therapy, a biological therapy is delivered to the intracardiac region to restore the ventricular rhythm that provides for a desirable hemodynamic performance.

The drug therapy includes delivering a pharmaceutical substance to the intracardiac region in or about the His bundle. In one embodiment, the drug therapy conditions the His bundle to facilitate the biological therapy. In one specific embodiment, the pharmaceutical substance prevents the degeneration of the His bundle that occurs when AV conduction is absent. In another embodiment, the drug therapy, or an additional drug therapy, is delivered subsequent to the biological therapy to enhance the biological therapy. The pharmaceutical substance includes one or more chemical agents. In one example, a growth factor is delivered to promote vessel growth in the intracardiac region, thereby increasing blood supply to that region.

The electrical therapy includes His bundle pacing, i.e., delivering cardiac pacing pulses to the intracardiac region in or about the His bundle. In one embodiment, the His bundle pacing conditions the intracardiac region to facilitate the biological therapy. In one specific embodiment, the His bundle pacing prevents the degeneration of the His bundle and maintains its normal electrical conduction characteristics. In one embodiment, the His bundle pacing enhances the drug therapy. In a further embodiment, the His bundle pacing is delivered subsequent to the biological therapy to enhance the biological therapy. Additionally, the His bundle pacing maintains or improves hemodynamic performance of the heart, such as increasing stroke volume and ventricular synchrony, at least until the biological therapy is successful. The maintained hemodynamic performance prevents ventricular remodeling and creates a physiological environment facilitating the biological therapy. The pacing mode for the His bundle pacing is selected from all available single chamber, dual chamber, and multi-chamber pacing modes, based on the need and the circumstances of a particular patient. In one embodiment, VVI or VVIR mode pacing is delivered to the intracardiac region with the His bundle treated as a ventricular pacing site. In another embodiment, in which a normal sinus rhythm is present, an atrial tracking pacing mode, such as VDD, VDDR, DDD, and DDDR, is applied with the His bundle treated as a ventricular pacing site. Other standard and custom pacing modes may also be applied, depending on the need and circumstances of each individual patient.

The biological therapy includes delivering a therapeutic biological substance to the intracardiac region in or about the His bundle. In one embodiment, the therapeutic biological substance includes a biologic pacemaker. In another embodiment, the therapeutic biological substance develops into a biologic pacemaker in the intracardiac region. The therapeutic biological substance includes one or more of cells, matrices, and gene products. More specifically, the therapeutic biological substance includes, but is not limited to, one or more of exogenous cells, a cloned pacemaker channel, cloned a or β subunits of the endogenous human pacemaker current (HCN2 or other HCN types), and stem cells containing HCN channel genes. Examples of such biological therapy are discussed in Qu et al., *J. Physiol.*, 526(3), 561-69 (2000), Qu et al., *Circ. Res.*, 89(1), e8-14(2001), Yu et al., *Circ. Res.*, 88(12), e84-87 (2001), and Shi et al., *Circ. Res.*, 85(1), e1-6 (1999)

Throughout this document, unless otherwise indicated, "intracardiac region" refers to the intracardiac region in or about the His bundle (AV bundle) or bundle branches. The drug therapy, electrical therapy, and biological therapy can be administrated each alone, in any combination, and/or in any order or sequence, depending on the particular need and conditions of an individual patient.

FIGS. 1A-D illustrate various embodiments of an implantable endocardial lead assembly. The lead assembly includes a steerable stylet 120 suitable for locating the His bundle by electrophysiological mapping, a hollow needle 134 suitable for intracardiac injection of the therapeutic biological substance, and an implantable endocardial pacing lead 100 (shown by its various embodiments including lead 100A and 100B). Lead 100 includes a lumen 114 accommodating a portion of stylet 120 or a portion of needle 134. Lumen 114 allows a stylet distal end 124 or a needle distal end 138 to reach the intracardiac region through lead 100. In this document, unless indicated otherwise, the term "distal end" refers to the portion of lead 100, stylet 120, or needle 134 that is to be disposed in the intracardiac region, and the term "proximal end" refers to the opposite end of lead 100, stylet 120, or needle 134.

FIG. 1A is an illustration of portions of lead 100A, which is one embodiment of lead 100. Lead 100A is a screw-in, unipolar endocardial lead providing an electrical connection between the intracardiac region and an implantable CRM device. Lead 100A includes an elongate lead body 102 having a lead distal end 108A and a lead proximal end 116. At or near lead distal end 108A, lead 100A includes an electrode 104, a fixation helix 106, and an osmotic drug collar 110. At lead proximal end 116, lead 100A includes a terminal pin 118. A conductor 112A electrically and mechanically connects electrode 104 and terminal pin 118. Lumen 114 extends throughout lead 100A and has a proximal opening at lead proximal end 116 and a distal opening at lead distal end 108A. It accommodates at least a portion of a flexible elongate object, and allows an end portion of that flexible elongate object to enter the proximal opening and exit from the distal opening. In one embodiment, the implantable CRM device includes a pacemaker. Electrode 104 allows the pacemaker to sense cardiac electrical activities from and delivering pacing pulses to the intracardiac region.

Lead 100A includes a conductor 112A formed by a multifilar wire coiled around a major portion of lumen 114 and connecting electrode 104 and terminal pin 118. In one embodiment, fixation helix 106 is mechanically connected to electrode 104. In a further embodiment, fixation helix 106 is also electrically connected to electrode 104, and is therefore a part of electrode 104. In one embodiment, fixation helix 106 is a retractable fixation. It advances or retracts in a rotating motion when terminal pin 118 is being rotated. The rotation is translated to fixation helix 106 through conductor 112A.

Figure 1B:
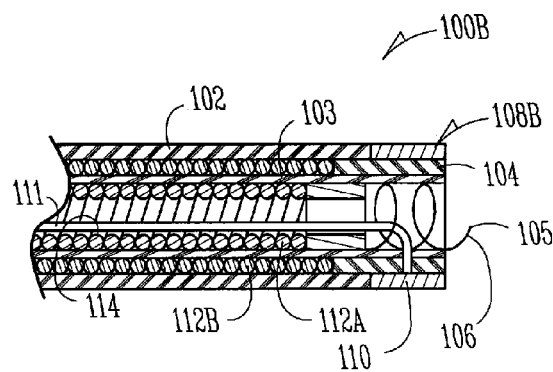
FIG. 1B is an illustration of an embodiment of portions of an implantable bipolar endocardial lead for pacing an intracardiac region.

FIG. 1B is an illustration of portions of lead 100B, which is another embodiment of lead 100. As illustrated in FIG. 1B, lead 100B is a bipolar lead providing for two separate electrical connections between the intracardiac region and an implantable CRM device. Terminal pin 118 for lead 100B includes two separate conductive portions that allow electrodes 104 and 105 to connect to the implantable CRM device separately. Lead 100B includes a first conductor 112A and a second conductor 112B. First conductor 112A is formed by a multifilar wire coiled around a major portion of lumen 114 and connecting electrode 104 and a first conductive portion of terminal pin 118. Second conductor 112B is formed by another multifilar wire coiled around a major portion of first conductor 112A and connecting electrode 105 and a second conductive portion of terminal pin 118. A tubular insulation layer 103 separates conductors 112A and 112B. In one embodiment, fixation helix 106 is mechanically and electrically coupled to conductor 112A, and includes a conductive tip forming electrode 105. In one embodiment, fixation helix 106 is a retractable fixation. It advances or retracts in a rotating motion when terminal pin 118 is being rotated. The rotation is translated to fixation helix 106 through conductor 112A.

Lumen 114 in lead 100 (100A or 100B) accommodates one of a portion of stylet 120 and a portion of needle 134, for the purposes of allowing access to the intracardiac region by stylet distal end 124 or needle distal end 138, respectively. In one embodiment, lumen 114 has a substantially uniform diameter throughout its length.

Drug collar 110 is incorporated into the distal end of lead 100 (distal end 108A of lead 100A or distal end 108B of lead 100B) and delivers the pharmaceutical substance including the one or more chemical agents. In one embodiment, drug collar 110 includes a drug reservoir containing the pharmaceutical substance and a means for controlled delivery of the pharmaceutical substance. In another embodiment, drug collar 110 includes the means for controlled delivery of the pharmaceutical substance, and the implantable CRM device includes the drug reservoir, which is in fluid communication with drug collar 110 via a passageway 111 within and extending through lead 100. In one embodiment, the means for controlled delivery includes an osmotic membrane such that the pharmaceutical substance is delivered by way of osmosis. One example of a drug delivery system including the drug reservoir containing the pharmaceutical substance and the means for controlled delivery of the pharmaceutical substance is discussed in U.S. patent application Ser. No. 10/246,249, "DEVICES AND METHODS TO STIMULATE THERAPEUTIC ANGIOGENESIS FOR ISCHEMIA AND HEART FAILURE," filed on Sep. 18, 2002, now issued as U.S. Pat. No. 6,915,169, assigned to Advanced Cardiovascular Systems, Inc., which is incorporated herein by reference in its entirety.

Examples of additional details about lead 100 such as lead 100A or 100B are discussed below with reference to FIGS. 6A, 6B, and 7.

Figure 1C:
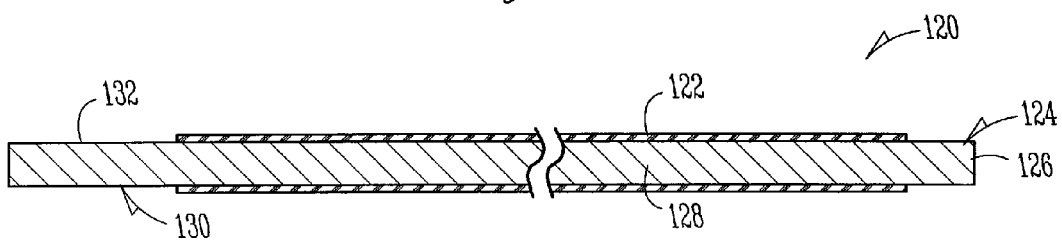
FIG. 1C is an illustration of an embodiment of a stylet accessing to the intracardiac region through the implantable endocardial lead of FIG. 1A or FIG. 1B.

FIG. 1C is an illustration of an embodiment of stylet 120. Stylet 120 is a steerable mapping stylet including a mapping electrode 126 at stylet distal end 124, a connector 132 at stylet proximal end 130, a conductor 128 electrically connecting mapping electrode 126 and connector 132, and a nonconductive shell 122 insulating at least a major portion of conductor 128. In one embodiment, mapping electrode 126, connector 132, and conductor 128 include a single conductor. Stylet 120 includes an insulated conductor with both distal and proximal ends exposed to allow electrical connection. That is, mapping electrode 126 includes a non-insulated portion of conductor 128 at about stylet distal end 124, and connector 132 includes another non-insulated terminal portion of conductor 128 at about stylet proximal end 130.

Examples of material of which nonconductive shell 122 is made include, but are not limited to, silicone, polyurethane, Teflon, and polytetrafluoroethylene (PTFE). Examples of material of which conductor 128 and connector 132 are each is made include, but are not limited to, stainless steel and alloys of nickel, titanium, cobalt, etc. Examples of material of which electrode 126 is made include, but are not limited to, one or more of platinum and iridium alloy.

Figure 1D:
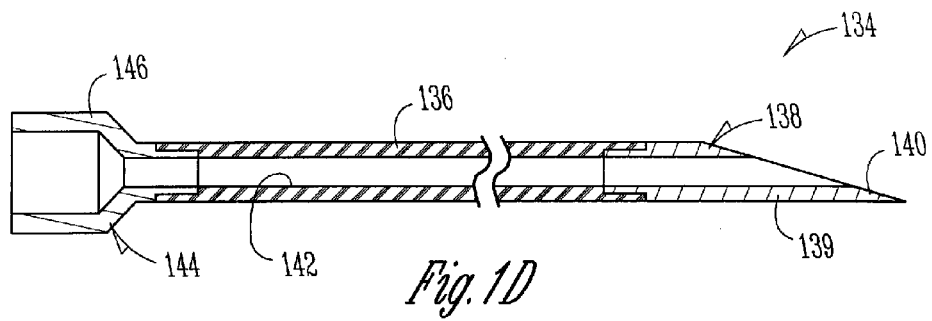
FIG. 1D is an illustration of an embodiment of a needle accessing to the intracardiac region through the implantable endocardial lead of FIG. 1A or FIG. 1B.

FIG. 1D is an illustration of an embodiment of a needle 134. Needle 134 is a hollow needle that allows for intracardiac injection of the pharmaceutical and/or therapeutic biological substance. Needle 134 includes a needle tip 140 at needle distal end 138, a needle connector 146 at needle proximal end 144, a flexible needle body 136 connecting needle tip 140 and needle connector 146, and a needle lumen 142 extending throughout needle 134 to allow passage of the pharmaceutical and/or therapeutic biological substance. In one embodiment, needle 134 includes a radiopaque marker 139 at needle distal end 138 to allow monitoring of the location of needle tip 140 inside a body using fluoroscopy.

In one embodiment, needle tip 140 is constructed of, by way of example, but not but way of limitation, one of stainless steel, stainless steel alloys, and nitinol. Needle body 136 is constructed of, by way of example, but not by way of limitation, one of Teflon, polyethylene terephthalate (PET), and polyurethane. Needle tip 140 includes a non-cutting tip, such as a conical tip, that is designed to avoid damages to lumen 114 of lead 100.

In one embodiment, needle lumen 142 has a substantially uniform diameter throughout its length. The diameter of needle lumen 142 is sufficient for the passage of the pharmaceutical and/or therapeutic biological substance.

Figure 2A:
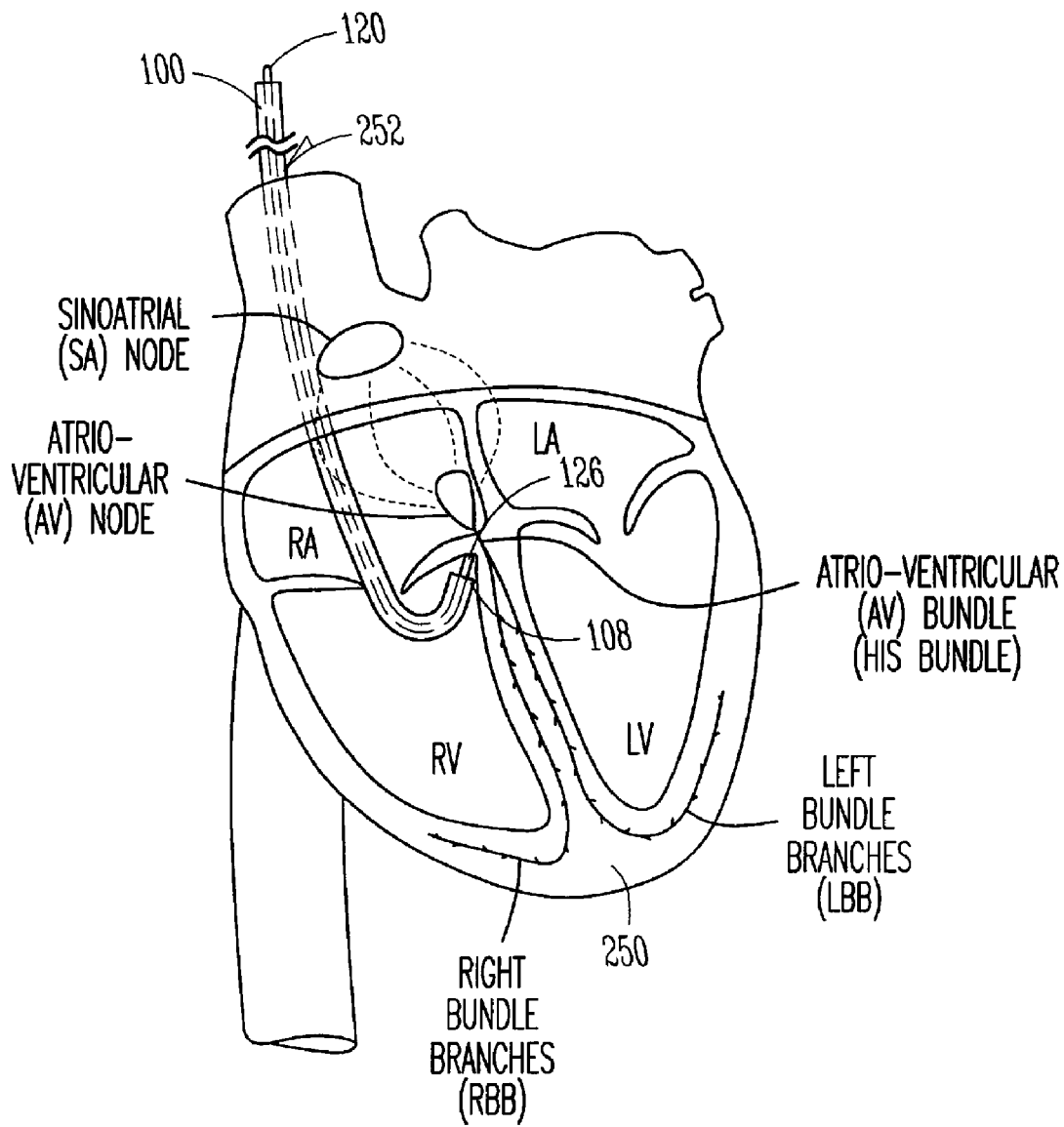
FIG. 2A is an illustration of an embodiment of an implantable endocardial lead assembly, with a mapping stylet, and portions of an environment in which it is used.

FIG. 2A is an illustration of an embodiment of an implantable endocardial lead assembly 252, including lead 100 and stylet 120, and portions of an environment in which it is used. In the drawing of this document, lead 100 includes a pacing lead such as lead 100A and lead 100B, and lead distal end 108 includes the distal end portion of lead 100, such as lead distal end 108A of lead 100A and lead distal end 108B of lead 100B, as discussed above with reference to FIGS. 2A and 2B. Lead assembly 252 is used for locating the His bundle in a heart 250 by electrophysiological mapping. The mapping allows the electrical therapy and the drug therapy to be delivered directly to the His bundle by accurately locating it. In FIG. 2A, lumen 114 of lead 100 accommodates a portion of stylet 120. Lead distal end 108 is disposed in a heart 250 near the His bundle. Stylet 120 is steered to move forward and backward relative to lead 100, through lumen 114 of lead 100, such that mapping electrode 126 is disposed outside of lead distal end 108 in a plurality of sites within the intracardiac region.

Figure 2B:
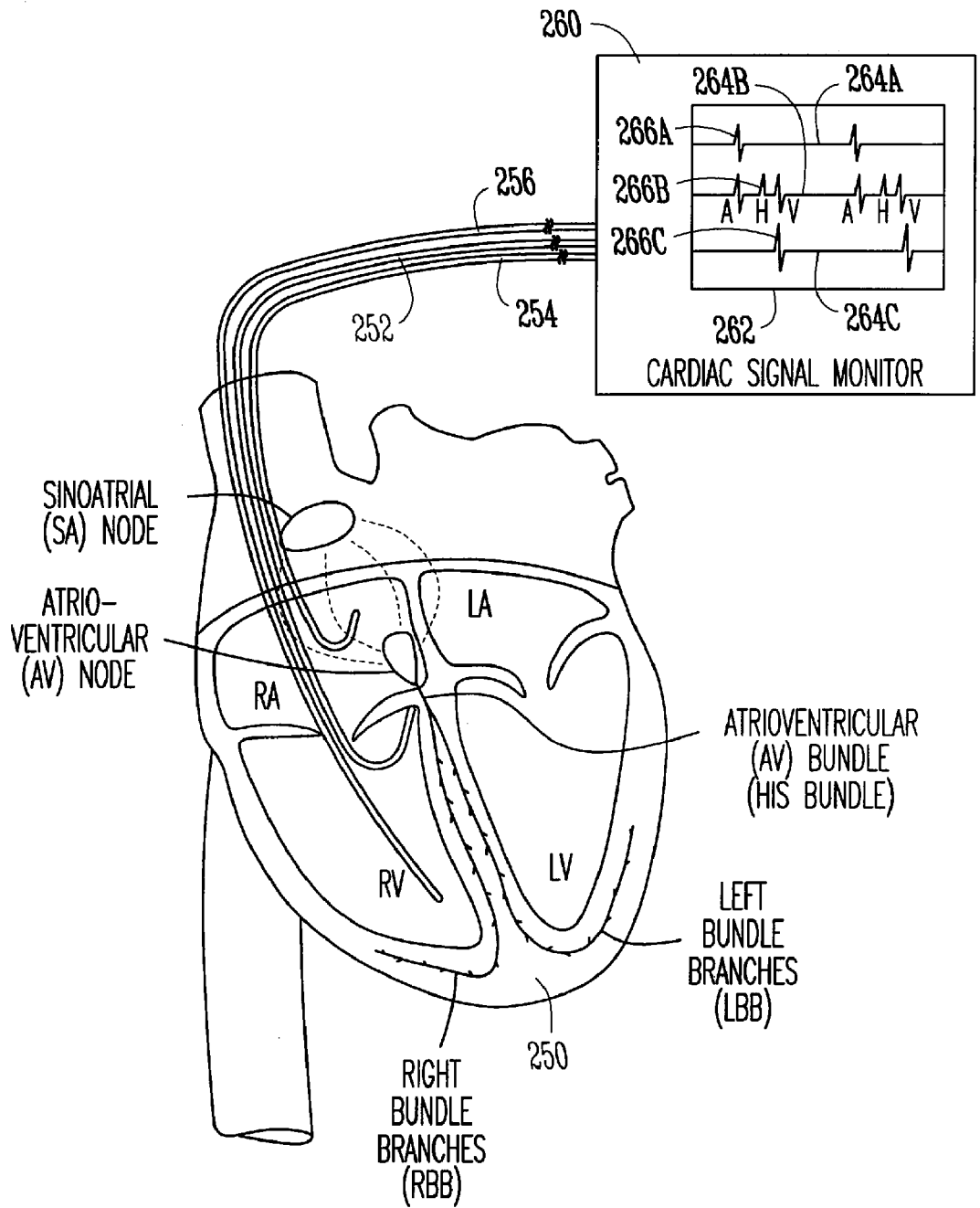
FIG. 2B is an illustration of an embodiment of an apparatus for locating the His bundle by electrophysiological mapping using the implantable endocardial lead assembly of FIG. 2A.

FIG. 2B is an illustration of an embodiment of an apparatus for locating the His bundle by electrophysiological mapping using lead assembly 252. The electrophysiological mapping includes a process of seeking a site where an electrical impulse as recorded from that site displays a known timing, amplitude, and/or morphological relationship with that electrical impulse as recorded from a known site. FIG. 2B illustrates an embodiment in which the His bundle is located by recording a His bundle electrogram as well as atrial and/or ventricular electrogram. The atrial and/or ventricular electrograms are used as references for the timing, amplitude, or morphological relationship between an event in the His bundle electrogram and the same event in the atrial and/or ventricular electrograms. In one specific embodiment, the drug and electrical therapies are delivered after an AV node ablation in a patient suffering atrial fibrillation. The His bundle is located by mapping before the ablation, when the AV conduction is still intact, and the His bundle can be located based on the known or expected conduction intervals between the atrium and the His bundle and between His bundle and the ventricle. In another specific embodiment, the His bundle is located subsequent to an AV block based on a retrograde Purkinje fibers-His bundle conduction.

In FIG. 2B, a mapping system includes lead assembly 252 (including lead 100 and stylet 120), an atrial lead 254 having at least one electrode in RA, and a ventricular lead 256 having at least one electrode in RV. Stylet 120, atrial lead 254, and ventricular lead 256 are connected to a cardiac signal monitor 260 that senses electrograms. One specific example of cardiac signal monitor 260 includes PRUCKA Cardio Lab EP System (model C-Lab Pro-800, GE Marquette Medical System). Cardiac signal monitor 260 includes a display 262 to present an RA electrogram 264A sensed via atrial lead 254, a His bundle electrogram 264B sensed via stylet 120, and an RV electrogram 264C sensed via ventricular lead 256. RA electrogram 264A includes events 266A indicative of RA depolarizations, referred to as RA events. RV electrogram 264C includes events 266C indicative of RV depolarizations, referred to as RV events, which are triggered by the electrical impulses which cause events 266A and are conducted through the His Bundle to the RV. His bundle electrogram 264B includes events 266B indicative of the AV conduction of the electrical impulses which cause events 266A, as recorded at the location of mapping electrode 126. In one embodiment, His bundle electrogram 264B includes A, H, and V waves. The A waves correspond to the RA depolarizations sensed by mapping electrode 126. The V waves correspond to the RV depolarizations sensed by mapping electrode 126. The H waves are events 266B. As illustrated in FIG. 2B, A, H, and V waves are identifiable by using the simultaneously displayed RA electrogram 264A and/or RV electrogram 264C as references. Stylet 120 provides for sensing of electrogram 264B in several sites in the general area where His bundle is likely located. In one embodiment, several pairs of conduction intervals are measured, with respect to the several sites, between adjacent events 266A and 266B, and between adjacent events 266B and 266C. The His bundle, or the site for delivering the intended pacing and drug therapy, is located by identifying one pair of the conduction intervals that agrees with the expected RA-His bundle conduction interval and His Bundle-RV conduction interval. In another embodiment, several conduction intervals are measured, with respect to the several sites, between adjacent events 266B and 266C. The His bundle, or the site for delivering the intended pacing and drug therapy, is located by identifying one of the conduction intervals that agrees with the expected His bundle-RV conduction interval. In one specific embodiment, an AV conduction interval is measured between RA and RV. In an alternative embodiment, ventricular lead 256 is disposed in heart 250 with at least one electrode in LV. All the embodiments discussed with respect to RV are applicable with RV substituted by LV. In one specific embodiment, an AV conduction interval is measured between RA and LV. In one embodiment, amplitudes of events 266B measured at the several sites are compared for locating or confirm the location of the His bundle. The one of the several sites associated with the largest events 266B amplitude is considered in or closest to the His bundle.

The atrium-His bundle conduction interval is generally expected to be about 60 ms to 120 ms. The His bundle-ventricle conduction interval is generally expected to be about 35 ms to 55 ms.

Figure 3:
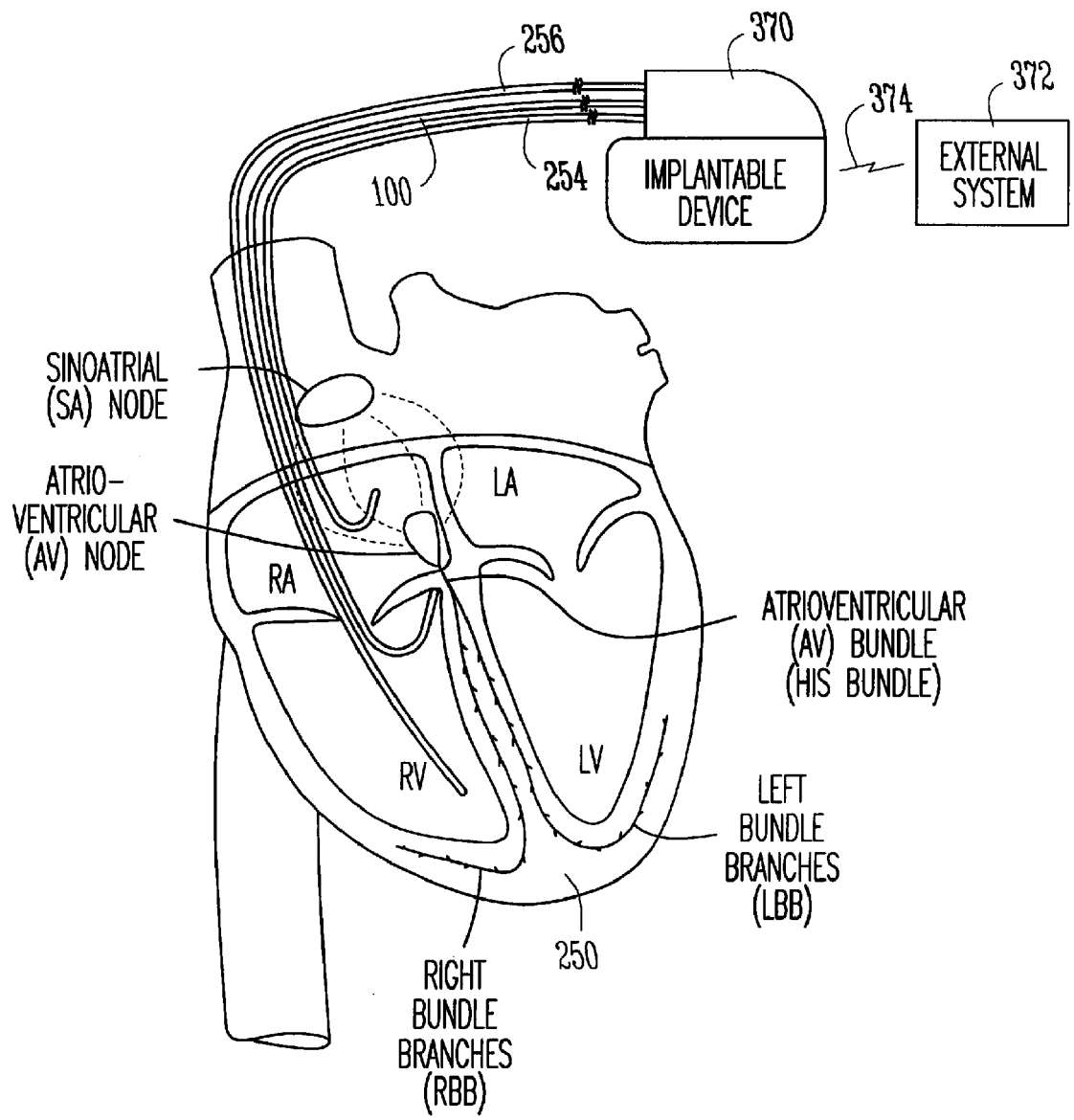
FIG. 3 is an illustration of an embodiment of a cardiac rhythm management system including the implantable endocardial lead of FIG. 1A or FIG. 1B connected to an implantable pacemaker.

FIG. 3 is an illustration of an embodiment of a CRM system including lead 100 connected to an implantable device 370 that provides for a pacing therapy. Implantable device 370 communicates with an external system 372 via a telemetry link 374. Implantable device 370 includes a cardiac pacemaker. In one embodiment, implantable device further includes a defibrillator. In one embodiment, external system 372 includes a programmer. In another system, external system 372 includes an advanced patient monitoring system such as discussed in U.S. patent application Ser. No. 10/323,604, "ADVANCED PATIENT MANAGEMENT FOR DEFINING, IDENTIFYING AND USING PREDETERMINED HEALTH-RELATED EVENTS," filed on Dec. 18, 2002, assigned to Cardiac Pacemakers, Inc., the specification of which is incorporated herein by reference in its entirety.

After the site for delivering the drug and/or electrical therapies is located, fixation helix 106 of lead 100 is screwed in to that site by rotating terminal pin 118, and stylet 120 is removed from lead 100. Lead 100 is then connected to implanted device 370 to allow the His bundle pacing. If the pacing mode used for the His bundle pacing requires RA sensing and/or pacing, atrial lead 254 remains connected to heart 250 and is also connected to implantable medical device 370. If the pacing mode used for the His bundle pacing requires RV or LV sensing and/or pacing, ventricular lead 256 remains connected to heart 250 and is also connected to implantable medical device 370.

In one embodiment, implantable device 370 includes a single chamber pacemaker capable of delivering VVI mode pacing (with the His bundle treated as a ventricular pacing site). In one further embodiment, implantable device 370 also includes a physiological sensor, such as an accelerometer or a respiration sensor, to support a rate adaptive pacing in the VVIR mode. In one embodiment, implantable device 370 includes a dual chamber or multi-chamber pacemaker capable of delivering either single chamber pacing such as VVI mode pacing or dual/multi-chamber pacing such as VDD and DDD mode pacing. In one further embodiment, implantable device 370 also includes a physiological sensor, such as an accelerometer or a respiration sensor, to support a rate adaptive pacing in pacing modes such as VVIR, VDDR, and DDDR. In one embodiment, the pacemaker includes other standard or custom pacing modes, to be selected based on the need and the circumstances of each individual patient.

The drug therapy is delivered by osmotic drug collar 110 at the distal end of lead 100. This includes releasing the pharmaceutical substance to the area surrounding osmotic drug collar 110, i.e., the intracardiac region in or near the His bundle. In one embodiment, the drug therapy enhances the therapeutic effect of the electrical therapy in conditioning the heart to facilitate an anticipated biological therapy. In another embodiment, the electrical therapy enhances the therapeutic effect of the drug therapy.

Figure 4A:
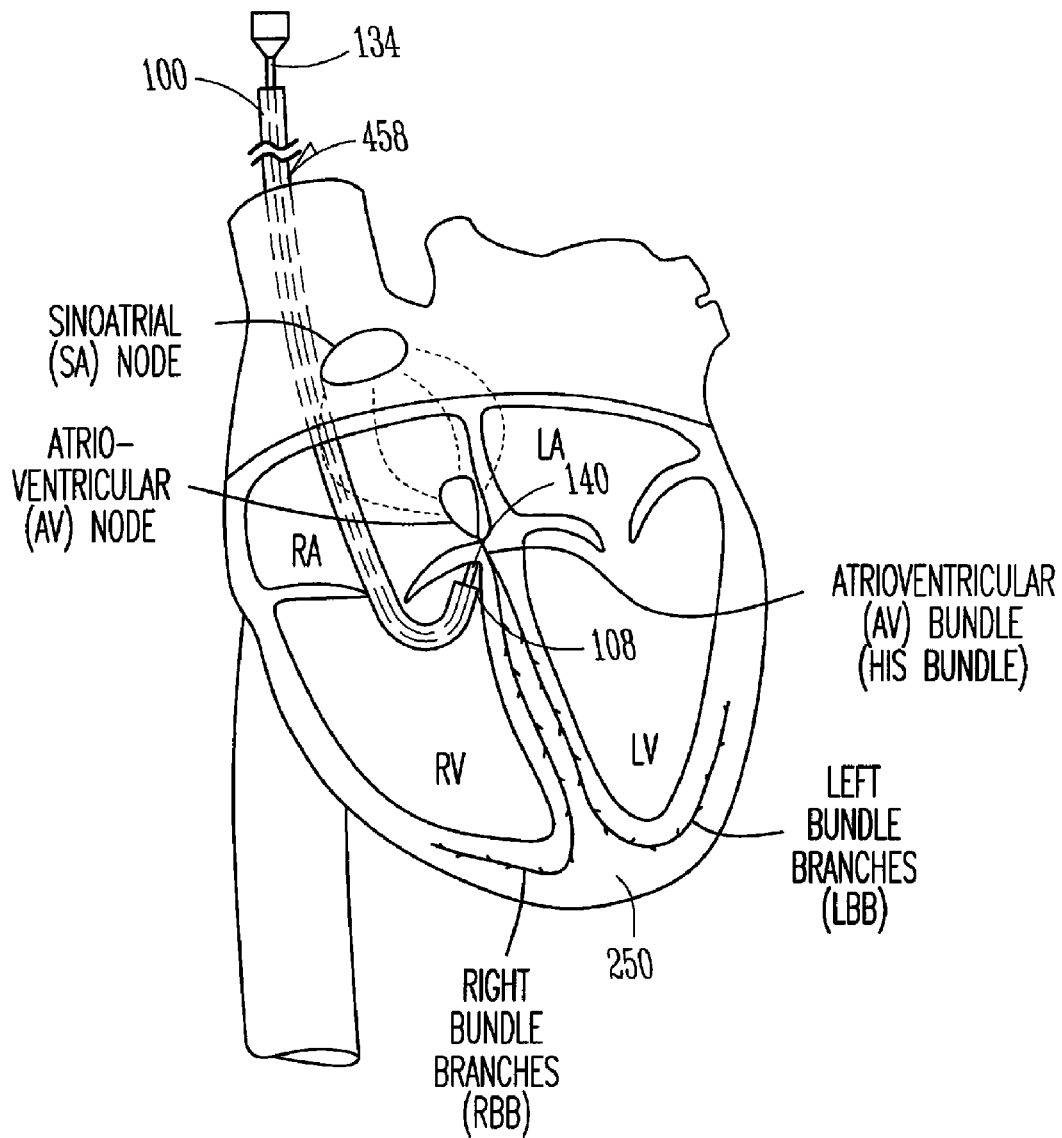
FIG. 4A is an illustration of an embodiment of an implantable endocardial lead assembly, with a needle, and portions of an environment in which it is used.

FIG. 4A is an illustration of an embodiment of an implantable endocardial lead assembly 458, including lead 100 and needle 134, and portions of an environment in which it is used. Lead assembly 458 is used for delivering the biological therapy to the intracardiac region in or about the His bundle. The delivery of the biological therapy includes injecting the biologic substance through needle 134. After the His bundle is located by the electrophysiological mapping, lead 100 is fixed to the site to which the drug therapy and/or the electrical therapy, as well as the biological therapy, are delivered. To inject the biological substance, needle 134 is advanced through lumen 114 of lead 100 until needle tip 140 extends beyond lead distal end 108 of lead 100 to enter cardiac tissue. In one embodiment, the needle tip is advanced to a predetermined point that is visible under fluoroscopy. In another embodiment, lead 100 and/or needle 134 include a needle stop structure to limit the extent to which needle tip can be extended beyond lead distal end 108. The biologic substance is then injected into needle proximal end 144 and forced through needle 134 to enter the intracardiac site.

Figure 4B:
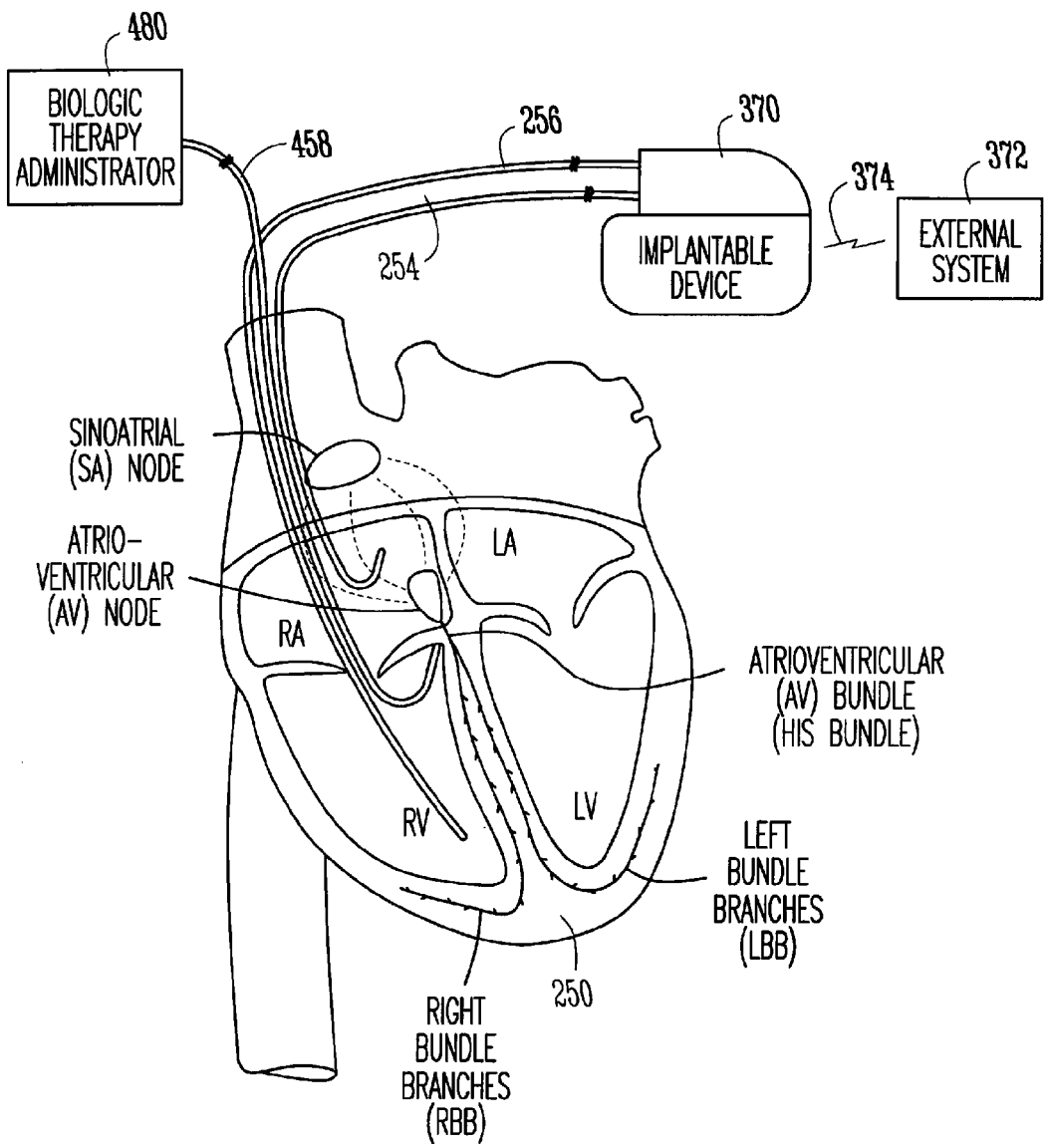
FIG. 4B is an illustration of an embodiment of an apparatus for delivering a biopacemaker therapy using the implantable endocardial lead assembly of FIG. 4A.

FIG. 4B is an illustration of an embodiment of an apparatus for delivering the biological therapy using lead assembly 458, including lead 100 and needle 134. In one embodiment, after the intracardiac region is treated by the drug and/or electrical therapies, the biological therapy is delivered to the intracardiac region surrounding lead distal end 108 of lead 100. In one embodiment, lead 100 is temporarily disconnected from implantable device 370 for the delivery of the biological therapy. Needle 134 is then advanced through lumen 114 until needle tip 140 penetrates into the tissue of the intracardiac region. Needle connector 144 is connected to a biological therapy administrator 480 from which the biological substance is delivered. In one embodiment, biological therapy administrator 480 includes a syringe.

In one embodiment, the purpose of delivering the biological therapy is to develop a biologic pacemaker in the intracardiac region in or about the His bundle in heart 250. This biologic pacemaker generates electrical impulses in a way similar to the SA node. The His bundle conducts the electrical impulses from the biologic pacemaker to the right bundle branch (RBB) and left bundle branch (LBB). The RBB and LBB then conduct the electrical impulses to the RV and LV, respectively, resulting in the synchronized contraction of the ventricles.

In one embodiment, after the delivery of the biological therapy, a drug therapy and/or an electrical therapy is delivered using the CRM system illustrated in FIG. 3. In one embodiment, after the delivery of the biological therapy, the CRM system remains in the patient and continues to deliver the drug and/or electrical therapies to the patient. The drug and/or electrical therapies enhance the biological therapy by stimulating the injected biological substance and by maintaining an intracardiac environment facilitating the development of the biologic pacemaker.

Figure 5:
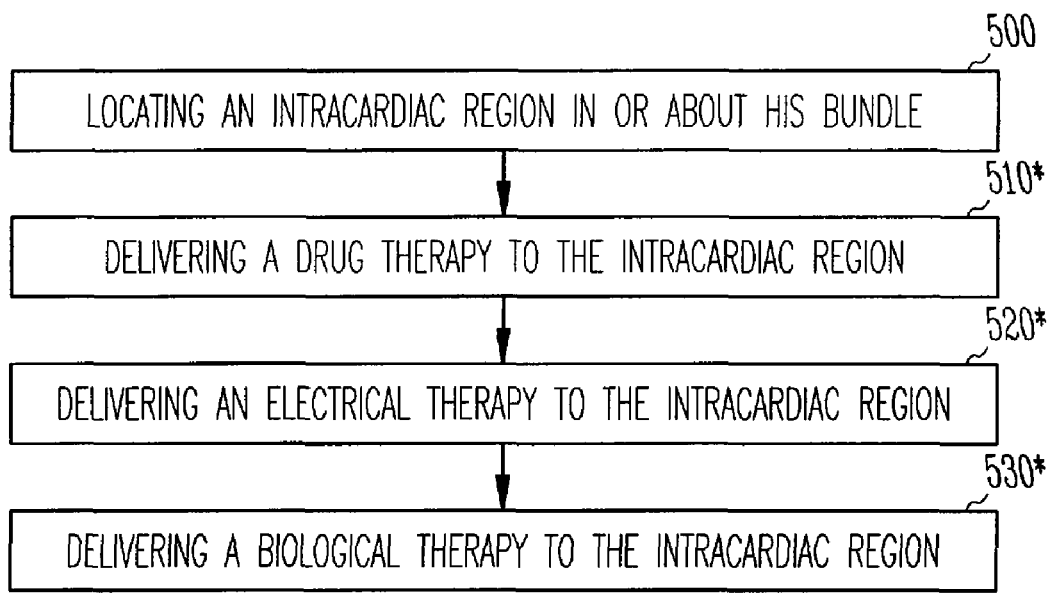
FIG. 5 is a flow chart illustrating a method for treating a heart by a biopacemaker therapy.

FIG. 5 is a flow chart illustrating a method for treating heart 250 using combined drug, electrical, and biological therapies. The method includes delivering the drug, electrical and/or biological therapies to the intracardiac region in or about the His bundle. An electrophysiological mapping is performed to locate the intracardiac region at 500. In one embodiment, the intracardiac region is located by using, for example, the apparatus illustrated in FIG. 2B, before an AV node ablation. Mapping electrode 126 is placed in a plurality of sites accessible with lead assembly 252. One site suitable for delivering the drug, electrical, and biological therapies, either being in the His bundle or the closest to the His bundle, is selected based on the amplitude and/or the timing of the electrical impulses recorded for each of the plurality of sites.

The drug therapy is delivered to the located intracardiac region at 510. In one embodiment, a pharmaceutical substance is delivered from osmotic drug collar 110 at lead distal end 108 of lead 100. The pharmaceutical substance treats the intracardiac region to facilitate the biological therapy.

The electrical therapy is delivered to the located intracardiac region at 520. In one embodiment, the electrical therapy includes His bundle pacing. In one embodiment, pacing pulses are delivered from implantable device 370 via lead 100.

The biological therapy is delivered to the located intracardiac region at 530. In one embodiment, a biological substance is delivered with lead assembly 458, i.e., through needle 134 advanced to the intracardiac region through lumen 114 of lead 100.

The drug, electrical, and biological therapies can be performed in different orders and may each be repeated after interruption, depending on each individual patient's needs and specific circumstances. In other words, steps 510, 520, and 530 in FIG. 5 do not denote any particular order or sequence. For example, before the biological therapy, the drug therapy and the electrical therapy can be delivered to condition the tissue to facilitate the biological therapy. After the biological therapy is delivered, the drug therapy and the electrical therapy can be delivered to enhance the biological therapy.

FIGS. 6A and 6B are detailed illustrations of one embodiment of the distal end of a bipolar pacing lead 600 as a specific embodiment of lead 100B. The design and construction of lead 600, including its detailed components, are generally applicable for lead 100A, with necessary modifications. FIG. 6A illustrates lead distal end 608 when lead 600 is in a retracted position. FIG. 6B illustrates a lead distal end 608 when lead 600 is in an extended position. As illustrated in FIGS. 6A and 6B, lead 600 includes a tip electrode and a ring electrode. The tip electrode includes a fixation helix 606, an electrode base 672, and an electrode collar 678 connecting fixation helix 606 and electrode base 672. Electrode base 672 and electrode collar 678 each have a tubular structure forming a portion of lumen 614. Fixation helix 606 allows lead distal end 608 to be affixed to the intracardiac region. Electrode base 672 is mechanically connected to conductor a 612A, such that when conductor 612A rotates, the electrode base 672 translates along an axis 660 of lead 600. In a further embodiment, electrode base 672 is formed of an electrically conductive material, such as metal, and is electrically connected to conductor 612A. Disposed about electrode base 672 are external threads 676, which allow electrode base 672 to rotate and translate fixation helix 606. Electrode base 672 is coupled with an outer threaded shell 674. The ring electrode includes electrode 675, which is electrically connected to a conductor 612B. An inner insulation 677 electrically insulates conductors 612A and 612B from each other. A lead body 602 provides for an outer insulation for the conductors.

In one embodiment, components of the tip and ring electrodes are all made of conductive materials such as metals. Examples of material of which fixation helix 606 is made include, but are not limited to, stainless steel, platinum-iridium, and titanium. Examples of material of which electrode base 672 is made include, but are not limited to, stainless steel alloys. Examples of material of which electrode collar 678 is made include, but are not limited to, stainless steel and platinum-iridium alloys. Examples of material of which electrode 675 is made include, but are not limited to, platinum-iridium alloys.

Lead 600 includes a drug collar 610 for delivering a pharmaceutical substance including the one or more chemical agents. In one embodiment, drug collar 610 includes a drug reservoir containing the pharmaceutical substance and a means for controlled delivery of the pharmaceutical substance. In another embodiment, drug collar 610 includes the means for controlled delivery of the pharmaceutical substance. Lead 600 includes a passageway providing for fluid communication between drug collar 610 and the implantable medical device to which lead 610 is connected.

Lead body 602 forms the outer shell for a major portion of lead 600. Examples of material of which the outer shell is made include, but are not limited to, silicone and polyurethane.

In one embodiment, conductors 612A and 612B each include a coiled multifilar wire. Examples of material of which the coiled multifilar wire is made include, but are not limited to, stainless steel, stainless steel alloy MP35N, titanium, and tantalum.

In one embodiment, a steroid collar 662 is disposed within lead distal end 608 of the lead 600. Steroid collar 662 includes a steroidal substance that releases into the intracardiac region after lead distal end 608 is placed in that region. The steroidal substance reduces inflammation that is a response to the invasion of lead 600 into the intracardiac region.

Outer threaded shell 674 includes internal threads 682. As the electrode base 672 rotates, external threads 676 engage with internal threads 682 and translate electrode base 672 along axis 660. In one embodiment, lead 600 includes a stop to prevent fixation helix 606 from over-extension. In one embodiment, a stop 670 on internal threads 682 blocks the rotation of external threads 676. Once external threads 676 reach stop 670, electrode base 672 can no longer be rotated and translated. This prevents fixation helix 606 from being over-extended into the tissue of the intracardiac region. In one embodiment, a stop 666 is formed on an outer shell 680 to block the movement of electrode collar 678.

In one embodiment, outer threaded shell 674 and/or outer shell 680 are each formed of polyetheretherketone (PEEK). In one embodiment, outer threaded shell 674 is formed of PEEK 150G, which has a low melt viscosity. For PEEK 150G, the melt viscosity ranges from about 0.12-0.18 KNs/m$^2$, and the tensile strength is greater than or equal to 90 MPa. In another embodiment, outer threaded shell 674 is formed of PEEK 450G, which has a standard melt viscosity. For PEEK 450G, the melt viscosity ranges from about 0.38-0.50 KNs/m$^2$, and the tensile strength is greater than or equal to 90 MPa. PEEK allows outer threaded shell 674 to be molded, extruded, or machined for tighter tolerances or providing precision structures. PEEK is a tough rigid thermoplastic material that is biocompatible.

Proximate to lead distal end 608 of lead 600 is a fluoroscopy ring 664, as a radiopaque marker disposed about fixation helix 106. In one embodiment, as fixation helix 606 is extended out from lead 600, electrode collar 678 translates toward fluoroscopy ring 664 until abutting a portion fluoroscopy ring 664, at which point the fixation helix 606 is fully extended. Electrode collar 678 and fluoroscopy ring 664 allow viewing, under fluoroscopy, of whether fixation helix 606 is fully extended.

In one embodiment, outer shell 680 provides a stop for the translation of electrode collar 678. Outer shell 680 is coupled with outer threaded shell 674. In one embodiment, epoxy 668 is disposed between outer threaded shell 674 and outer shell 680. In one embodiment, epoxy 668 includes a blend of two different epoxies. The two different epoxies include EPOTEK® 353ND and EPOTEK® 353ND-T made by Epoxy Technology. They are mixed in the ratio of 1 part EPOTEK® 353ND to 1.75 parts EPOTEK® 353ND-T. Epoxy 668 is cured at a temperature of 150° C. for one hour.

FIG. 7 is a detailed illustration of one embodiment of a lead proximal end 716 of lead 600 (as a specific embodiment of lead 100B). Lead proximal end 716 includes a terminal pin 718, which is mechanically and electrically coupled to conductor 612A. Terminal pin 718 provides the electrical connection between implantable device 370 and the tip electrode of lead 600 though conductor 612A. A connective crimp tube 787 reinforces the connection between terminal pin 718 and conductor 612A. As terminal pin 718 is rotated, conductor 612A rotates, thereby rotating electrode base 672, electrode collar 678, and fixation helix 606. Terminal pin 718 has a tubular structure that forms a proximal portion of lumen 614.

Lead 600 further includes an outer terminal ring 796 that is electrically coupled to conductor 612B through a conductive collar 789 to provide the electrical connection between implantable device 370 and the ring electrode (675) of lead 600 though conductor 612B. An insulator sleeve 798 is disposed over at least a portion of terminal pin 718, to insulate terminal pin 718 from outer terminal ring 796. In one embodiment, sleeve 798 rotates with outer terminal ring 796. In one embodiment, sleeve 798 is coupled to terminal pin 718 with a snap-fit connection. In another embodiment, sleeve 798 is also coupled to outer terminal ring 796 with a snap-fit connection. In one embodiment, sleeve 798 includes a shoulder 790. Shoulder 790 is engaged with a recess 794 of terminal pin 718, and prevents terminal pin 718 from moving axially. In one embodiment, shoulder 790 includes an annular shoulder disposed about the circumference of sleeve 798, which allows terminal pin 718 to rotate relative to outer terminal ring 796. The annular shoulder engages within an annular recess disposed within the circumference of terminal pin 718. In another embodiment, sleeve 798 further includes at least one recess 788 disposed adjacent to shoulder 790. Recess 788 receives a shoulder 786 of terminal pin 718. In another embodiment, sleeve 798 further includes a stop 792 for outer terminal ring 796. Terminal pin body 791 provides increased axial strength to the connection between lead 600 and implantable device 370.

Terminal pin 718 and outer terminal ring 796 are each made of conductive materials such as metals. Examples of material of which terminal pin 718 is made include, but are not limited to, stainless steel, titanium, and platinum-iridium. Examples of material of which terminal ring 796 is made include, but are not limited to, stainless steel, titanium, and platinum-iridium.

Sleeve 798 is formed of non-conductive material. In one embodiment, sleeve 798 is formed of PEEK. In one embodiment, sleeve 798 is formed of PEEK 150G. In another embodiment, sleeve 798 is formed of PEEK 450G. The PEEK allows sleeve 798 to be molded, extruded, or machined for tighter tolerances or providing precision structures.

Lumen 614 extends along axis 600 throughout lead 600, and has a substantially circular cross-section perpendicular to axis 600. As illustrated in FIGS. 6A, 6B, and 7, lumen 614 is formed directly by the tip electrode of lead 600, conductor 612, and terminal pin 718. Lumen 614 has a distal opening at lead distal end 608 and a proximate opening at lead proximal end 616. In one embodiment, the substantially circular cross-section has a substantially uniform diameter throughout lead 600. The diameter is of a size allowing passage of stylet 120 and needle 134 (one at a time).

Generally, metals used for components of lead 600, as illustrated in FIGS. 6A. 6B, and 7, include, but are not limited to, stainless steel, titanium, niobium, platinum-iridium alloys, other alloys such as elgiloy and nickel/titanium alloys. Non-metal materials used for components of lead 600, as illustrated in FIGS. 6A. 6B, and 7, include, but are not limited to, silicone, polyurethane, polydimethyls, siloxanes, and PEEK.

Other embodiments of the detailed structure and elements of lead 600 are available by adopting and/or modifying existing lead structures and elements to include lumen 614. Examples of such existing lead structures and elements are discussed in U.S. Pat. No. 6,141,594, "SINGLE PASS LEAD AND SYSTEM WITH ACTIVE AND PASSIVE FIXATION ELEMENTS," U.S. Pat. No. 6,463,334, "EXTENDABLE END RETRACTABLE LEAD," U.S. patent application Ser. No. 10/264,494, "EXTENDABLE AND RETRACTABLE LEAD HAVING A SNAP-FIT TERMINAL CONNEC- TOR," filed Oct. 4, 2002, all assigned to Cardiac Pacemakers, Inc., which are incorporated herein by reference in their entirety.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable endocardial pacing lead assembly for locating and delivering a pacing stimulus to a His bundle of a patient, the lead assembly comprising:
   a steerable stylet having a stylet distal end and a stylet proximal end, the steerable stylet including:
      a mapping electrode at the stylet distal end;
      a connector at the stylet proximal end; and
      a conductor electrically coupled between the mapping electrode and the connector;
   an implantable lead configured to be implanted in a patient and including:
      an elongate lead body having a lead proximal end and a lead distal end;
      a connector assembly at the proximal end of the lead body configured for coupling the lead to an implantable device configured to deliver therapy to the patient, the connector assembly including a rotatable terminal pin;
      a conductor coil extending within the lead body and mechanically and electrically coupled to the terminal pin;
      an extendable and retractable helical electrode at or near the lead distal end for sensing cardiac electrical activities and delivering pacing pulses, wherein the extendable and retractable electrode is rotatable and operable as a fixation helix and is coupled to the conductor coil; and
      a lumen within and extending through the lead body, the lumen including a proximal opening at about the lead proximal end and a distal opening at about the lead distal end, the lumen adapted to accommodate at least a portion of the steerable stylet and to allow the stylet distal end to enter the proximal opening and extend from the distal opening.

2. The lead assembly of claim 1, wherein the steerable stylet comprises a nonconductive shell insulating at least a portion of the conductor.

3. The lead assembly of claim 2, wherein the mapping electrode comprises a first terminal portion of the conductor at about the stylet distal end, the first terminal portion of the conductor not insulated by the nonconductive shell.

4. The lead assembly of claim 3, wherein the connector comprises a second terminal portion of the conductor at about the stylet proximal end, the second terminal portion of the conductor not insulated by the nonconductive shell.

5. The lead assembly of claim 1, wherein the implantable lead further comprises a drug delivery device at or near the lead distal end for delivering a pharmaceutical substance.

6. The lead assembly of claim 5, wherein the drug delivery device comprises a silicone polymeric collar to contain the pharmaceutical substance.

7. The lead assembly of claim 6, wherein the drug delivery device comprises an osmotic membrane and a drug reservoir containing the pharmaceutical substance.

8. The lead assembly of claim 7, wherein the pharmaceutical substance comprises one or more agents preventing a degeneration of a cardiac conductive system.

* * * * *